(12) United States Patent
Cimino

(10) Patent No.: US 6,585,745 B2
(45) Date of Patent: Jul. 1, 2003

(54) ULTRASONIC CUTTING AND COAGULATION KNIFE USING TRANSVERSE VIBRATIONS

(75) Inventor: William W. Cimino, Louisville, CO (US)

(73) Assignee: Sound Surgical Technologies LLC, Louisville, CO (US)

( * ) Notice: Subject to any disclaimer, the term of this patent is extended or adjusted under 35 U.S.C. 154(b) by 44 days.

(21) Appl. No.: 09/776,007

(22) Filed: Feb. 2, 2001

(65) Prior Publication Data

US 2001/0034532 A1 Oct. 25, 2001

Related U.S. Application Data

(60) Provisional application No. 60/179,951, filed on Feb. 3, 2000.

(51) Int. Cl.[7] .............................................. A61B 17/32
(52) U.S. Cl. ...................................................... 606/169
(58) Field of Search ................................ 606/169, 167; 604/22

(56) References Cited

U.S. PATENT DOCUMENTS

| 3,086,288 A |   | 4/1963  | Balamuth ...................... 30/272 |
| 3,526,219 A |   | 9/1970  | Balamuth ....................... 128/2 |
| 3,636,943 A |   | 1/1972  | Balamuth ................... 128/24 A |
| 4,136,700 A |   | 1/1979  | Broadwin ..................... 128/305 |
| 4,634,420 A |   | 1/1987  | Spinosa ......................... 604/72 |
| 5,047,043 A | * | 9/1991  | Kubota et al. ............... 606/169 |
| 5,156,143 A | * | 10/1992 | Bocquet et al. ............. 601/108 |
| 5,222,937 A | * | 6/1993  | Kagawa ........................ 604/22 |
| 5,261,922 A |   | 11/1993 | Hood ........................... 606/169 |
| 5,324,299 A | * | 6/1994  | Davison et al. ............. 606/167 |
| 6,077,285 A | * | 6/2000  | Boukhny ....................... 604/22 |
| 6,228,046 B1 | * | 5/2001  | Brisken ......................... 604/22 |
| 6,254,622 B1 | * | 7/2001  | Hood ........................... 606/169 |
| 6,309,400 B2 | * | 10/2001 | Beaupre ....................... 606/169 |
| 6,328,751 B1 | * | 12/2001 | Beaupre ....................... 606/169 |
| 6,402,769 B1 | * | 6/2002  | Boukhny ....................... 604/22 |

* cited by examiner

Primary Examiner—Danny Worrell
(74) Attorney, Agent, or Firm—Merchant & Gould P.C.

(57) ABSTRACT

An ultrasonic frequency surgical dissecting device including a handpiece with a surgical blade that vibrates in a direction transverse to a long axis passing through the handpiece and blade for improved cutting and coagulation.

21 Claims, 7 Drawing Sheets

ULTRASONIC CUTTING AND COAGULATION KNIFE USING TRANSVERSE VIBRATIONS

This application claims the benefit of provisional patent application Ser. No. 60/179,951 filed Feb. 3, 2000.

FIELD OF THE INVENTION

The present invention relates to improvements in surgery and, in particular, an ultrasonic surgical device and method with improved cutting and coagulation effects.

BACKGROUND

A steel scalpel makes a fine incision which damages only the tissues that are actually cut by the scalpel. However, steel scalpel incisions have no inherent coagulation effect, i.e., the cut tissues bleed until the incision is closed and natural coagulation takes place. Electrosurgical devices utilize high-frequency electrical currents to cut and coagulate tissues. Compared to steel scalpel incisions, electrosurgical incisions have a significant coagulation effect due to the heat generated in the tissues by the high-frequency electrical currents. However, electrosurgical incisions necessarily cause thermal tissue damage, specifically near and around the line of the incision. In general, this approach cannot be used in delicate areas, such as adjacent important nerves, which must remain undamaged after the surgery.

Ultrasonic frequency cutting and coagulation devices are well-known. See, e.g., U.S. Pat. Nos. 3,086,288 (Balamuth), 3,636,943 (Balamuth), 5,324,299 (Davidson), and 5,261,922 (Hood). All of these devices utilize longitudinal ultrasonic vibrations to accomplish tissue cutting and coagulation. Longitudinal vibrations are vibrations that are substantially parallel to the long axis passing through the respective surgical handpiece and surgical tip. As illustrated, for example in FIG. 1, the ultrasonic vibratory motion generated in the surgical blade or tip 2 attached to the surgical handpiece 1 of these devices is substantially parallel to the long axis 3 passing through the handpiece and tip. Because these devices utilize longitudinal ultrasonic vibratory motion, the motion of the blade or tip tends to be into and out of the tissue plane, in effect poking deeper into the tissue than one might desire. As illustrated in FIG. 2, this occurs because, the surgical handpiece 1 and tip 2 are typically held at an angle in the range of ±45 degrees relative to a normal 8 passing through the plane of animal tissue being operated upon. (See FIG. 2.) The longitudinal vibratory poking causes unnecessary bleeding and does not optimally utilize the coagulation capability inherent in the ultrasonic surgical device. Coagulation generally occurs only when the vibrating surgical blade or tip contacts the tip such that the vibratory motion of the surgical blade or tip is generally parallel to the direction of the incision in the plane of the tissue being operated upon. As illustrated for example in FIG. 3, this occurs when the surgical handpiece 1 and tip 2 are oriented so that the long axis 3 and the blade vibration are generally parallel to the tissue plane. In effect, this occurs by laying the surgical handpiece on the tissue—a difficult surgical procedure, at best—especially when working at depth through a small incision.

Accordingly, there is a need for an improved surgical device, particularly an improved ultrasonic frequency vibratory scalpel or dissection device that provides improved coagulation effects and minimizes tissue damage.

The present invention is an improved ultrasonic frequency vibrating scalpel or dissection device that increases coagulation capability and causes minimal tissue damage.

SUMMARY

The ultrasonic frequency vibrating dissecting device disclosed herein utilizes transverse vibrations to provide cutting and coagulation. An ultrasonic motor is disclosed that is able to generate and directly drive the transverse vibrations.

More specifically, the present invention includes a surgical handpiece with a surgical blade that vibrates at ultrasonic frequencies for cutting and coagulating animal tissue, the surgical handpiece and surgical blade comprising a long axis passing through the surgical handpiece and surgical blade; a most distal portion of the surgical blade that is disposed away from the surgical handpiece for contacting tissue of a patient; and the most distal portion of the surgical blade having a vibratory motion that is substantially perpendicular to the long axis.

BRIEF DESCRIPTION OF THE DRAWINGS

More specifically, FIG. 1 depicts the relative vibratory motion of a typical prior art ultrasonic surgical device.

FIG. 2 shows the usual surgical orientation of the device of FIG. 1 relative to the animal tissue being treated.

FIG. 3 shows another theoretical orientation of the device of FIG. 1 which might be utilized to minimize tissue damage and increase blood coagulation.

DETAILED DESCRIPTION OF THE INVENTION AND THE PREFERRED EMBODIMENT

Figure 1:
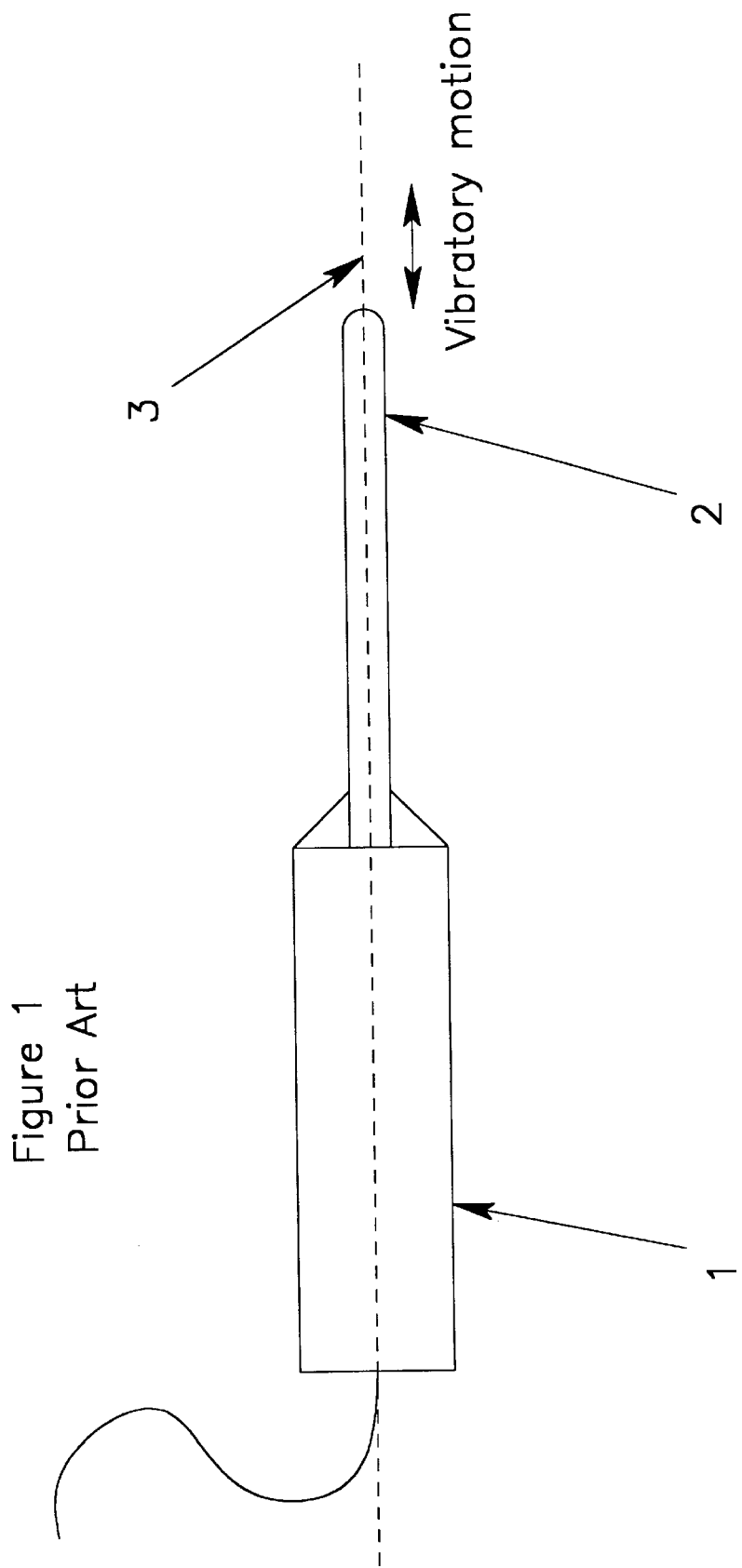
FIGS. 1 through 3 illustrate a typical "prior art" device.
Figure 2:
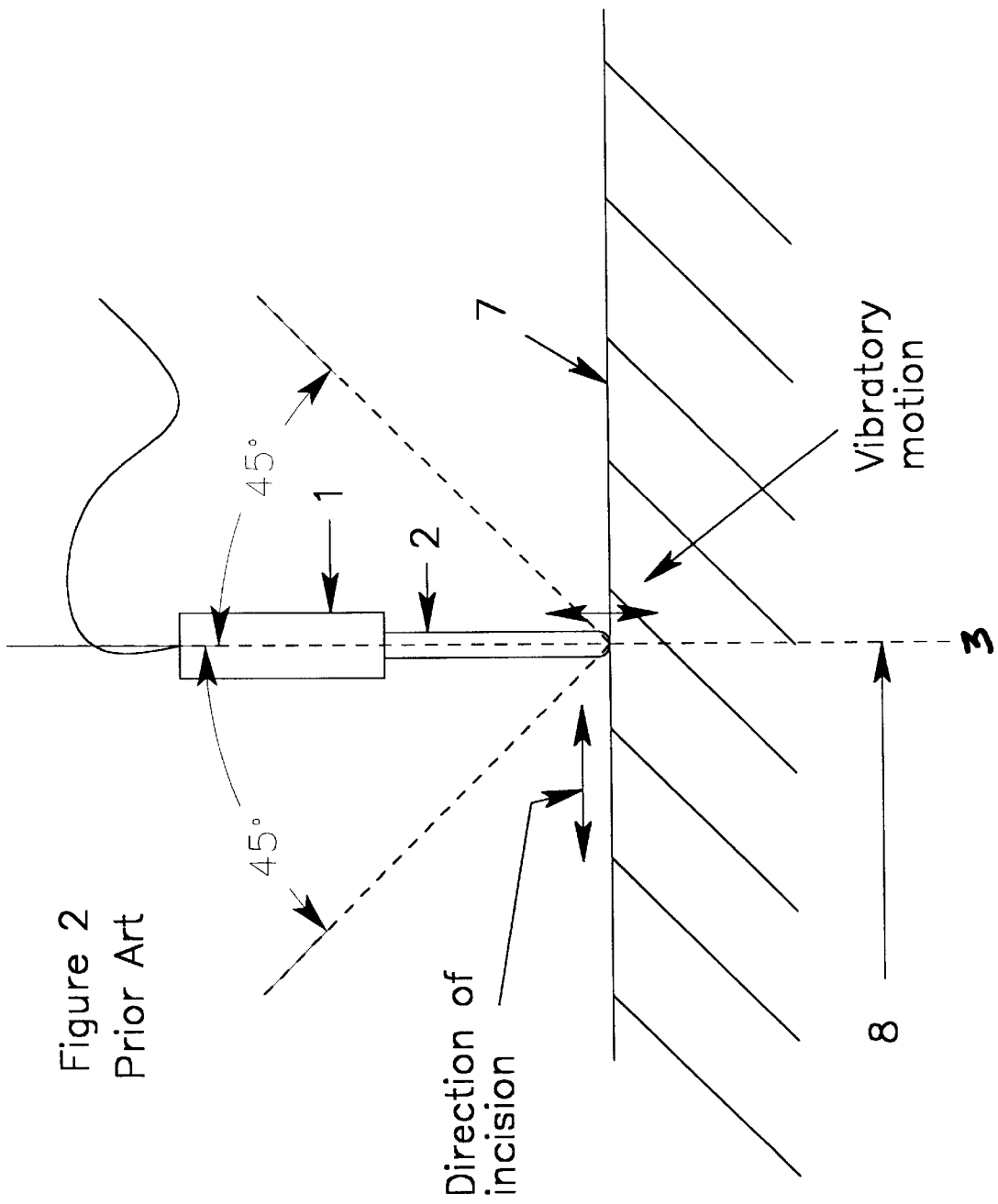
Figure 3:
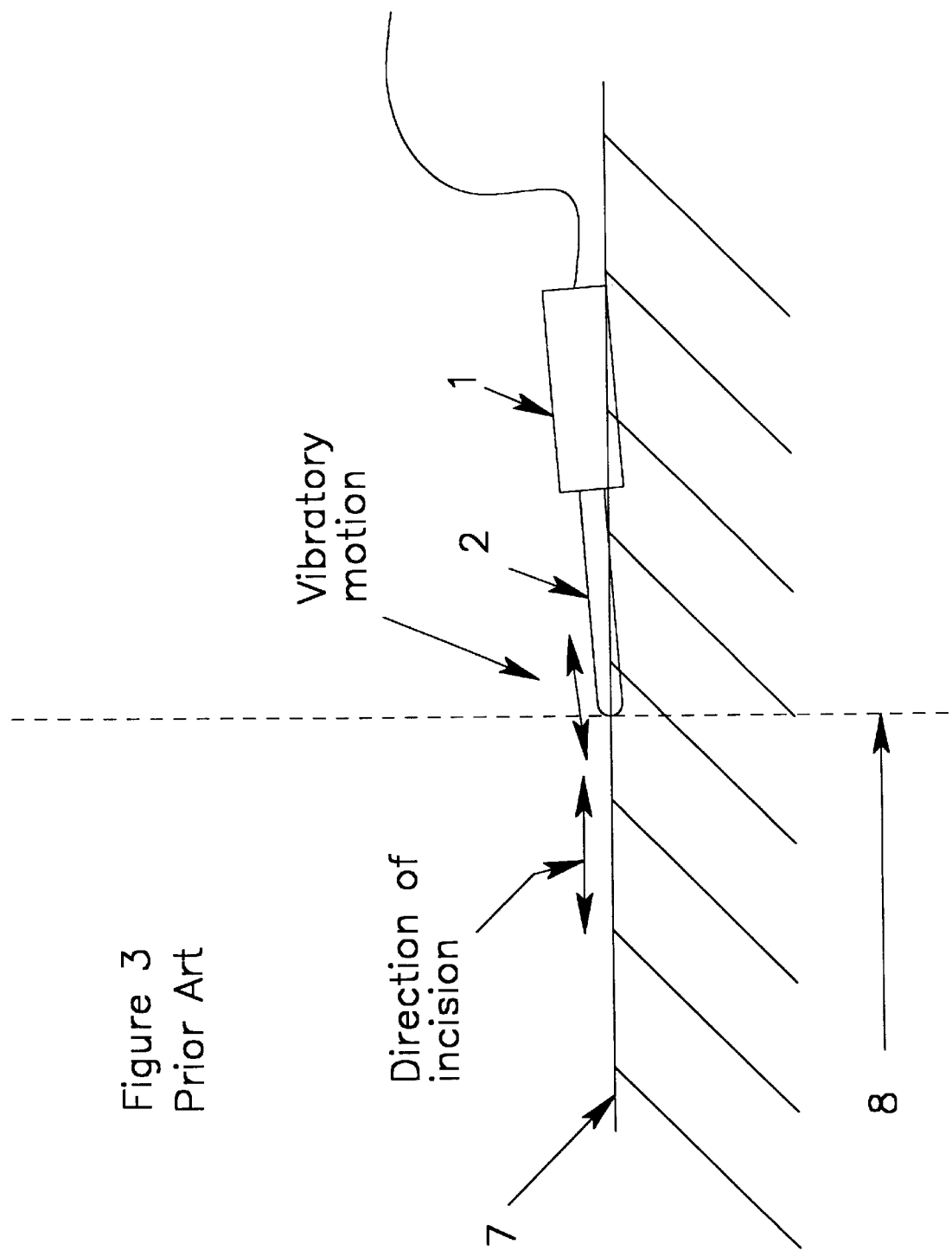
Figure 4:
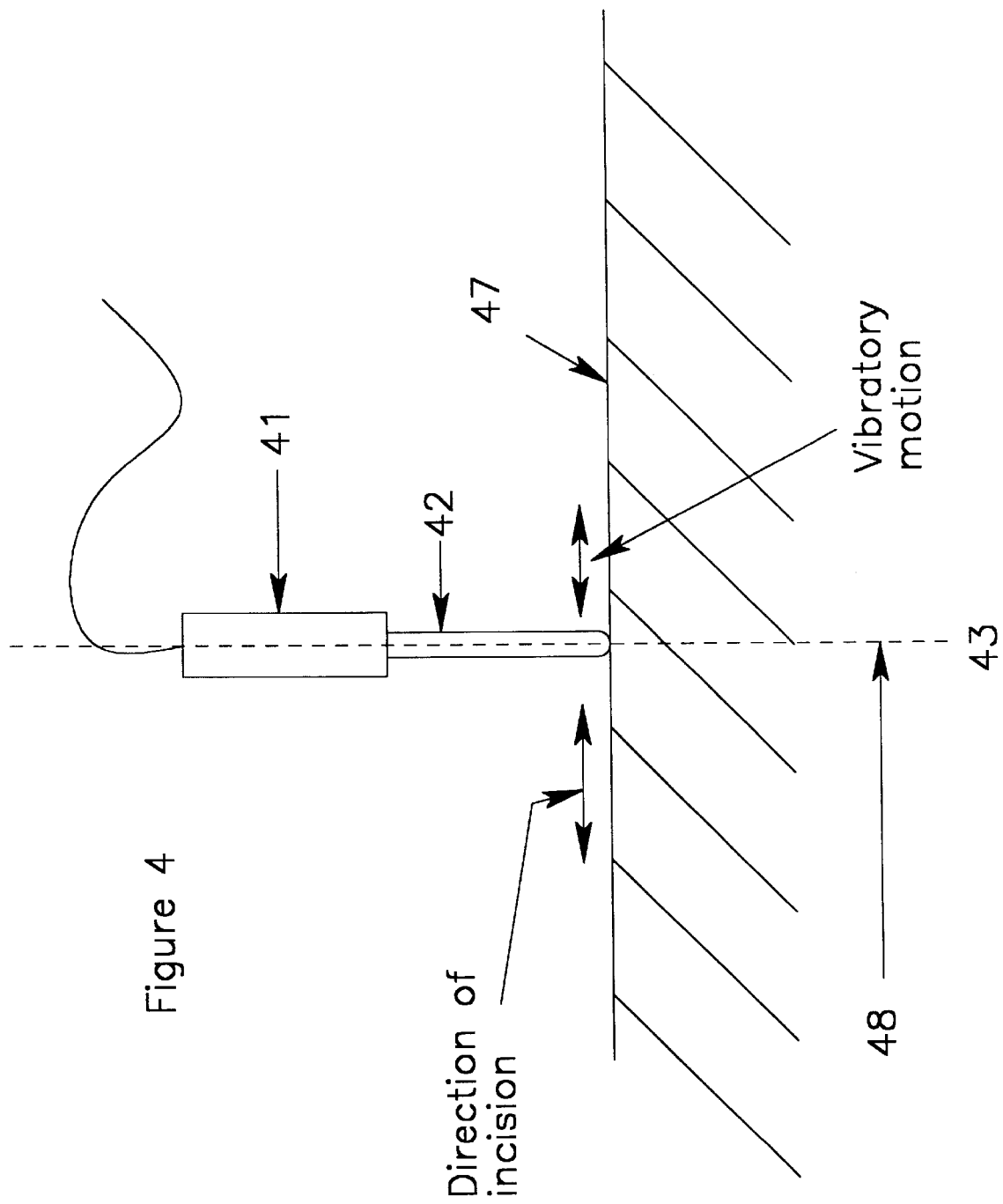
FIG. 4 shows one form of ultrasonic surgical device in accordance with the present invention.

Transverse vibrations are vibrations that are, in general, substantially perpendicular to the long axis of the surgical handpiece and surgical blade or tip. (See FIG. 4.) With transverse vibrations the vibratory motion of the surgical blade or tip is generally and substantially parallel to the direction of the incision in the tissue plane when the surgical handpiece is held in a typical operating position as shown in FIG. 4. Thus, the poking into and out of the tissue plane is eliminated and a substantial frictional effect is created that significantly increases coagulation.

The prior art does not teach effective transverse ultrasonic motion in a surgical device. U.S. Pat. No. 4,136,700 (Broadwin) has an ultrasonic surgical tool for neurosurgery that is used to fragment and remove tumor tissue. The device uses longitudinal vibrations connected through an angle to a tool tip such that 'transverse' vibrations are created. The vibrations are 'transverse' with respect to an axis passing through the tool tip but are in fact parallel to the long axis of the surgical handpiece as shown clearly by the arrows in FIG. 4 of the drawings of that patent. Thus, the 'transverse' vibrations disclosed in this patent do not address the aforementioned issues, namely that if the device is used in a typical surgical fashion, the tool tip would be poking into and out of the tissue plane. U.S. Pat. No. 4,634,420 (Spinosa) has 'lateral' vibrations that are used in combination with longitudinal vibrations to form an elliptical pattern. No method or mechanism is disclosed with which to generate or cause the 'lateral' vibrations to occur in a longitudinally vibrating surgical handpiece and blade. Similarly, U.S. Pat. No. 3,526,219 (Balamuth) has 'transverse' vibrations that are generated simultaneously with longitudinal vibrations. No method or mechanism is disclosed with which to generate or cause the 'transverse' vibrations to occur simultaneously in a longitudinally vibrating surgical handpiece. Indeed, the most recent prior art, e.g., U.S. Pat. No 5,261,922, mentioned previously, teaches away from the present invention, specifically noting that transverse motions of the surgical tip result in unwanted "whipping" that may lead to premature mechanical failure.

As illustrated in FIG. 4, the present invention is an ultrasonic frequency vibrating instrument for tissue cutting and coagulation that includes handpiece 41 and surgical blade 42. The surgical handpiece and surgical blade have a hypothetical centrally located long axis 43 that passes through the surgical handpiece and the surgical blade and uses transverse vibrations of the surgical blade, i.e., vibratory motions substantially perpendicular to a long axis 43 passing through the surgical handpiece and surgical blade. As illustrated in FIG. 4, the device is used by making an incision in the same plane as the vibratory motion. The surgical blade does not poke in and out of the tissue plane and generates an improved coagulation effect along the incision. This is achieved even when the long axis 43 is aligned perpendicular to the plane of tissue 47 being operated on. The transverse vibratory motion also facilitates the making of an incision in the same plane.

The surgical handpiece 41 has an ultrasonic motor that preferably is fabricated using PZT ceramic discs. The preferred PZT is a PZT-8 material. The PZT discs expand and contract when electrical energy is applied to their surfaces using electrodes and wires. The electrode is preferable fabricated using beryllium copper, with thickness of 0.001 to 0.003 inches. The ultrasonic motor in the present invention causes a bending motion by contracting on one side and expanding on the opposite side. This can be accomplished by a least two different methods.

Figure 6:
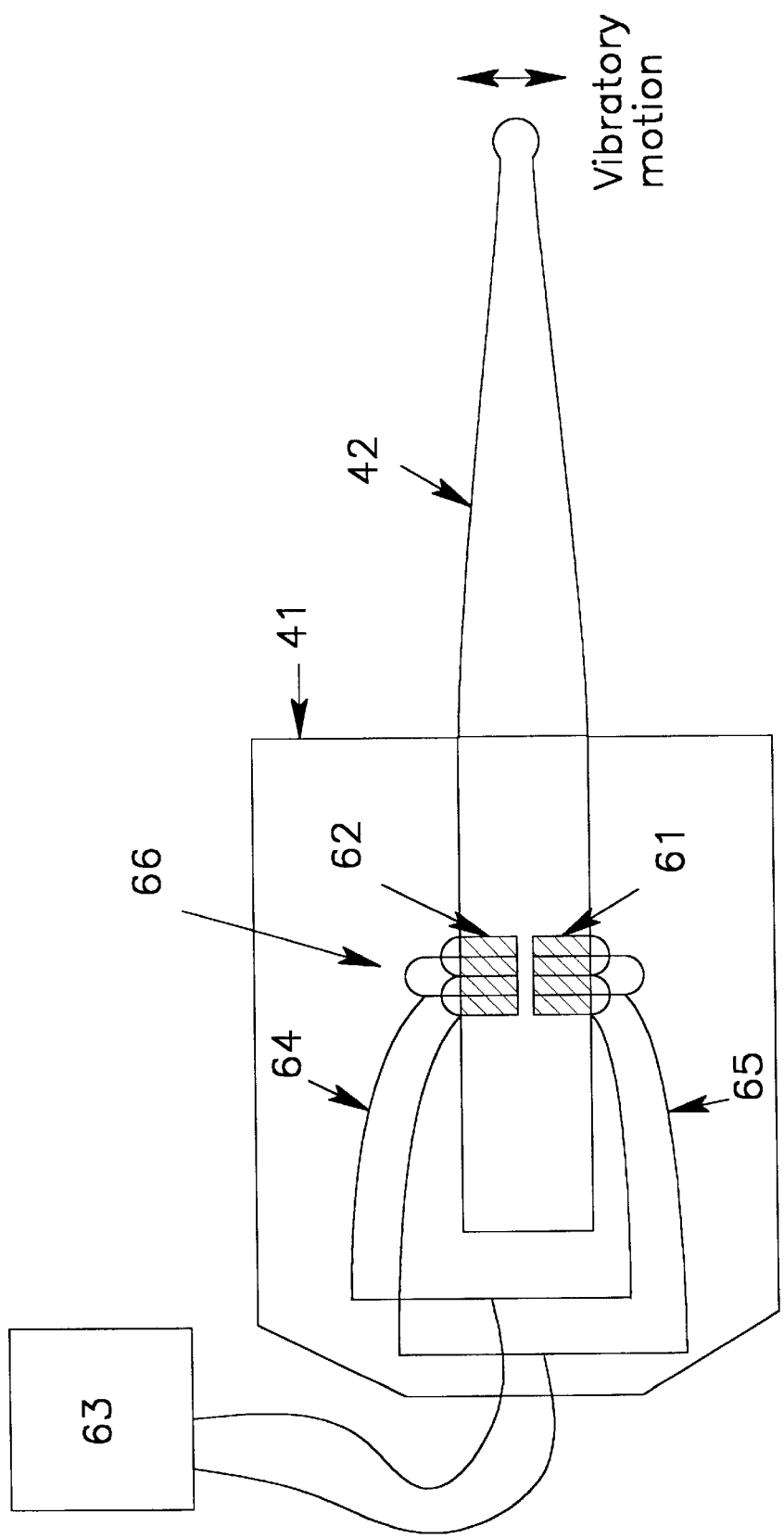
FIG. 6 shows one form of electrode configuration for an ultrasonic motor generating transverse vibrations in accordance with the present invention.

The first method is to use "split electrodes." This is shown in FIG. 6 which depicts this form of electrode configuration for an ultrasonic motor 66 to generate transverse vibrations. The motor is housed in handpiece 41 and drives ultrasonic surgical blade 42. As depicted in the drawing each half, 61 and 62, is comprised of four PZT elements (shown by cross-hatching), although other numbers of elements could be employed. The respective halves 61 and 62 of the PZT discs receive electrical voltages from power source 63 through electrodes 64 and 65, resulting in contraction on one half and expansion on the opposite half. Alternation of the voltage causes transverse vibration of the blade 42 in the directional plane shown.

Figure 7:
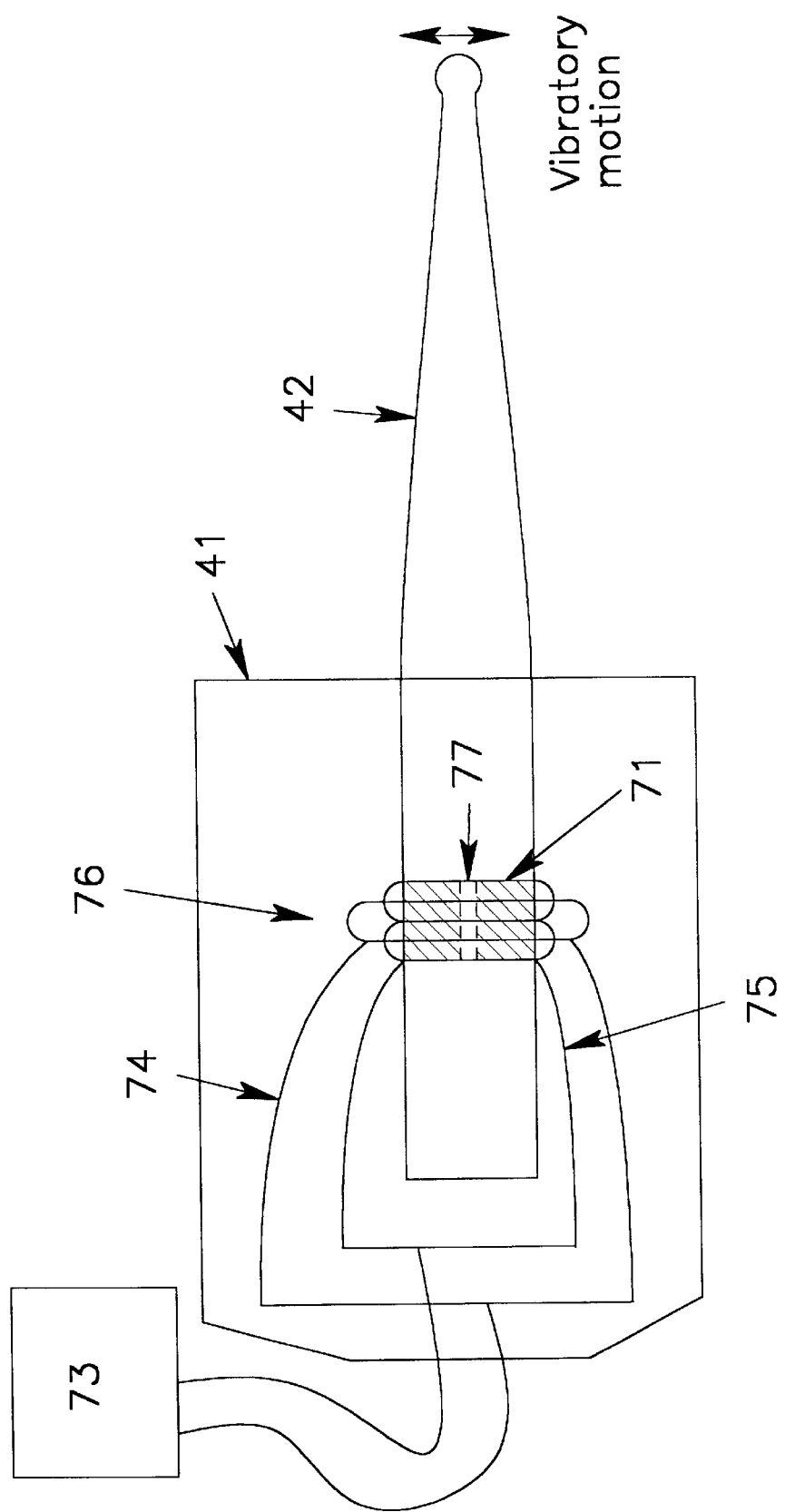
FIG. 7 shows a preferred form of electrode configuration for an ultrasonic motor generating transverse vibrations in accordance with the present invention.

The second method is to polarize the PZT disc material such that respective halves have opposite polarity. This is shown in FIG. 7 which depicts motor 76 configured to generate transverse vibrations. Again, the motor is housed in handpiece 41 to drive blade 42 in a transverse plane. Using this approach electrodes 74 and 75 are attached so that they are common to the entire faces of the PZT elements 71 as shown in the Figure. These elements are arranged in a stack with a hole 77 in the center. Four elements are depicted in FIG. 7 although other numbers of elements could be employed. Again, when an electrical voltage from power source 73 is applied to the PZT elements, one side contracts and the opposite side expands. By alternating the voltages the motor vibrates blade 42 in a transverse direction as depicted in FIG. 7. The second method is the preferred method because split electrodes are difficult to manufacture and assemble.

The surgical handpiece is connected to an ultrasonic generator that supplies electrical energy to the surgical handpiece and ultrasonic motor for conversion to vibratory motion. The surgical handpiece and surgical blade have a preferred resonant frequency. Typically, the range of vibratory frequency is between 10 kHz and 100 kHz. The ultrasonic generator provides electrical energy to the surgical handpiece and surgical blade such that vibration occurs primarily and substantially at the preferred resonant frequency.

Figure 5:
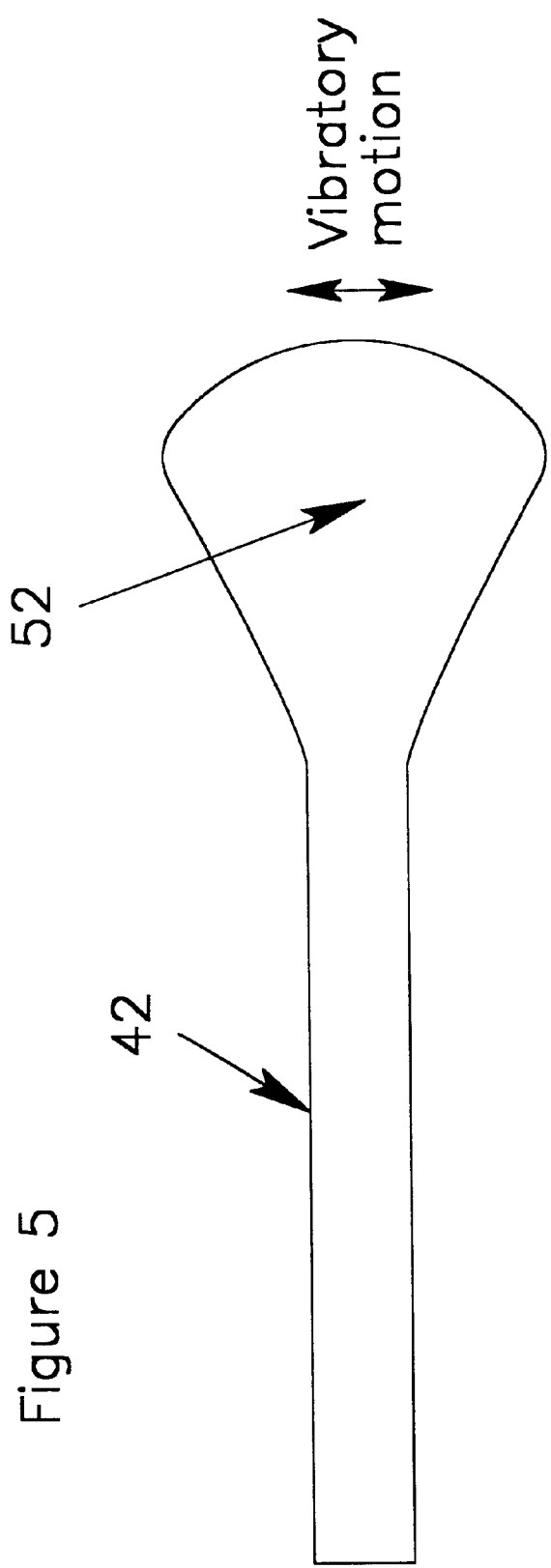
FIG. 5 is a top view of a preferred form of surgical knife in accordance with the present invention.

One preferred form of surgical knife 42 employed in the current invention is shown in FIG. 5. This is a top view of the knife; a side view would show a flat configuration in the tip area 52. In use the knife would be vibrated in the direction of the arrows shown in FIG. 5.

What is claimed is:

1. A surgical handpiece with a surgical blade that vibrates at ultrasonic frequencies for cutting and coagulating animal tissue, the surgical handpiece and surgical blade comprising:
   a long axis passing through the surgical handpiece and surgical blade;
   a most distal portion of the surgical blade that is disposed away from the surgical handpiece for contacting tissue of a patient; and
   the most distal portion of the surgical blade having a vibratory motion that is substantially perpendicular to the long axis.

2. A surgical handpiece with a surgical blade that vibrates at ultrasonic frequencies for cutting and coagulating animal tissue, the surgical handpiece and surgical blade comprising:
   a long axis passing through the ultrasonic surgical handpiece and surgical blade; an ultrasonic motor being located within the surgical handpiece and aligned along the long axis;
   a most distal portion of the surgical blade that is disposed away from the surgical handpiece for contacting tissue of a patient; and
   the most distal portion of the surgical blade having a vibratory motion that is substantially perpendicular to the long axis, the vibratory motion generated by the ultrasonic motor and conducted to the surgical blade.

3. A surgical handpiece with a surgical blade that vibrates at ultrasonic frequencies for cutting and coagulating animal tissue, the surgical handpiece and surgical blade comprising:
   a long axis passing through the surgical handpiece and surgical blade;
   a dividing plane passing through the surgical handpiece and surgical blade that includes the long axis;
   an ultrasonic motor located within the ultrasonic surgical handpiece and aligned along the long axis for generating transverse vibrations;
   a positive side of the ultrasonic motor and a negative side of the ultrasonic motor as defined by the dividing plane, the positive side that expands when the negative side contracts and vice versa;
   a most distal portion of the surgical blade that is disposed away from the surgical handpiece for contacting tissue of a patient; and
   a vibratory motion of the most distal portion of the surgical blade that is substantially perpendicular to the long axis and in a plane that includes the long axis and that is perpendicular to the dividing plane.

4. A surgical handpiece with a surgical blade that vibrates at ultrasonic frequencies for cutting and coagulating animal tissue, the surgical handpiece and surgical blade comprising:
- a long axis passing through the surgical handpiece and surgical blade;
- a most distal portion of the surgical blade that is disposed away from the surgical handpiece for contacting tissue of a patient; and
- a vibratory motion of the most distal portion of the surgical blade that is substantially perpendicular to the long axis to provide a substantial cutting and coagulation effect.

5. The apparatus of claim 3 wherein the ultrasonic vibratory frequency is between 10 kHz and 100 kHz.

6. The apparatus of claim 2 wherein the distal portion of the surgical blade comprises a tip that is flat and has a general shape that is wider at the most distal portion than at its base.

7. The apparatus of claim 3 wherein the ultrasonic motor comprises PZT discs, with a first set of electrodes attached to the positive side of the ultrasonic motor and a second set of electrodes attached to the negative side of the ultrasonic motor so that an opposite alternating voltage is applied to the positive and negative sides of the ultrasonic motor causing the generation of transverse vibrations.

8. The apparatus of claim 3 wherein the ultrasonic motor comprises PZT discs, with a first polarization on the positive side of the ultrasonic motor and an opposite polarization on the negative side of the ultrasonic motor and a set of electrodes placed between the PZT discs so that transverse vibrations are generated when an alternating voltage is applied to the electrodes.

9. A method of using a surgical handpiece and surgical blade, the method comprising:
- applying a distal tip of the surgical blade to the tissue of a patient; and
- vibrating the distal tip of the surgical blade substantially perpendicular to a long axis, the long axis passing through the surgical handpiece and surgical blade, and cutting and coagulating the tissue of the patient.

10. The method of claim 9 wherein vibrating of the distal tip occurs at a frequency between 10 kHz and 100 kHz.

11. The method of claim 9 wherein the distal tip is flat and has a general shape that is wider at the most distal portion than at its base.

12. The method of claim 9 wherein vibrating of the distal tip is caused by applying opposite alternating current to the positive and negative sides of an ultrasonic motor comprising PZT discs, with a first set of electrodes attached to the positive side of the ultrasonic motor and a second set of electrodes attached to the negative side of the ultrasonic motor.

13. The method of claim 9 wherein vibrating of the distal tip is caused by applying an alternating voltage to the electrodes of an ultrasonic motor comprising PZT discs, with a first polarization on the positive side of the ultrasonic motor and an opposite polarization on the negative side of the ultrasonic motor and a set of electrodes placed between the PZT discs.

14. The apparatus of claim 1 wherein the ultrasonic vibratory frequency is between 10 kHz and 100 kHz.

15. The apparatus of claim 1 wherein the surgical blade comprises a tip that is flat and has a general shape that is wider at the most distal portion than at its base.

16. The apparatus of claim 2 wherein the ultrasonic vibratory frequency is between 10 kHz and 100 kHz.

17. The apparatus of claim 3 wherein the surgical blade comprises a tip that is flat and has a general shape that is wider at the most distal portion than at its base.

18. The apparatus of claim 17 wherein the shape of the distal portion of the surgical blade is curved.

19. The apparatus of claim 17 wherein the ultrasonic vibratory frequency is between 10 kHz and 100 kHz.

20. The apparatus of claim 19 wherein the ultrasonic motor comprises PZT discs, with a first set of electrodes attached to the positive side of the ultrasonic motor and a second set of electrodes attached to the negative side of the ultrasonic motor so that an opposite alternating voltage is applied to the positive and negative sides of the ultrasonic motor causing the generation of transverse vibrations.

21. The apparatus of claim 19 wherein the ultrasonic motor comprises PZT discs, with a first polarization on the positive side of the ultrasonic motor and an opposite polarization on the negative side of the ultrasonic motor and a set of electrodes placed between the PZT discs so that transverse vibrations are generated when an alternating voltage is applied to the electrodes.

* * * * *